United States Patent
Yamin et al.

(10) Patent No.: US 11,931,543 B2
(45) Date of Patent: Mar. 19, 2024

(54) IV SET COMPONENT WITH PRIMING FUNCTION

(71) Applicant: CareFusion 303. Inc., San Diego, CA (US)

(72) Inventors: Leyla Yamin, San Diego, CA (US); Kelly Kloster Hon, Del Mar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 311 days.

(21) Appl. No.: 17/223,729

(22) Filed: Apr. 6, 2021

(65) Prior Publication Data

US 2022/0313900 A1    Oct. 6, 2022

(51) Int. Cl.
*A61M 5/14*       (2006.01)
*A61M 5/168*      (2006.01)

(52) U.S. Cl.
CPC ...... *A61M 5/1411* (2013.01); *A61M 5/16881* (2013.01); *A61M 2005/1402* (2013.01)

(58) Field of Classification Search
CPC ............ A61M 5/1411; A61M 5/16881; A61M 5/16804; A61M 2005/1402; A61M 2039/224; A61M 2039/229; A61M 2039/2473; A61M 2039/248; A61M 2039/2486; A61M 2039/2493; A61M 39/223; A61M 39/22; A61M 39/24
See application file for complete search history.

(56) References Cited

U.S. PATENT DOCUMENTS

| | | | |
|---|---|---|---|
| 4,046,696 A * | 9/1977 | Mouwen | B01D 35/147 210/431 |
| 4,325,368 A | 4/1982 | Kaemmerer | |
| 5,364,371 A | 11/1994 | Kamen | |
| 2011/0276031 A1* | 11/2011 | Hoang | A61M 5/1411 604/82 |

OTHER PUBLICATIONS

International Search Report and Written Opinion for Application No. PCT/US2022/022385 dated Jul. 15, 2022, 64 pages.

* cited by examiner

*Primary Examiner* — Nathan R Price
*Assistant Examiner* — Anh Bui
(74) *Attorney, Agent, or Firm* — Morgan, Lewis & Bockius LLP

(57) ABSTRACT

Drip chambers, burettes and other IV set components are described herein. An IV set component described herein comprises a chamber body, an inlet portion, and a disk valve. The chamber body defines a chamber volume and an outlet. The chamber volume is in fluid communication with the outlet. The inlet portion is coupled to the chamber body, the inlet portion defining an inlet, a priming port, a drip port. The inlet is in fluid communication with the priming port and the drip port, and the priming port and the drip port are each in fluid communication with the chamber volume. The disk valve is coupled to the inlet portion. The disk valve is movable to direct flow from the inlet to the priming port in a first position and to direct flow from the inlet to the drip port in a second position.

12 Claims, 3 Drawing Sheets

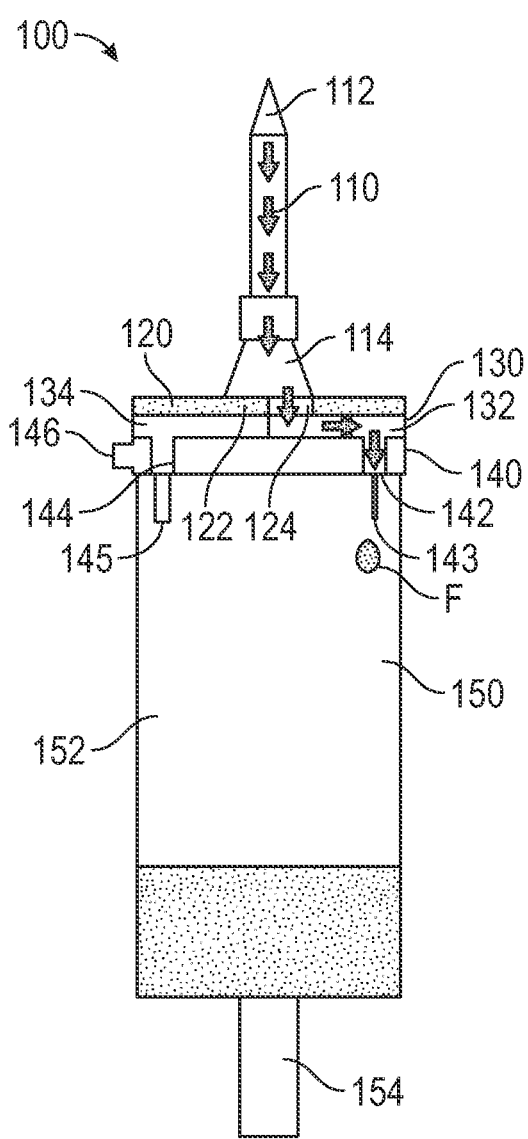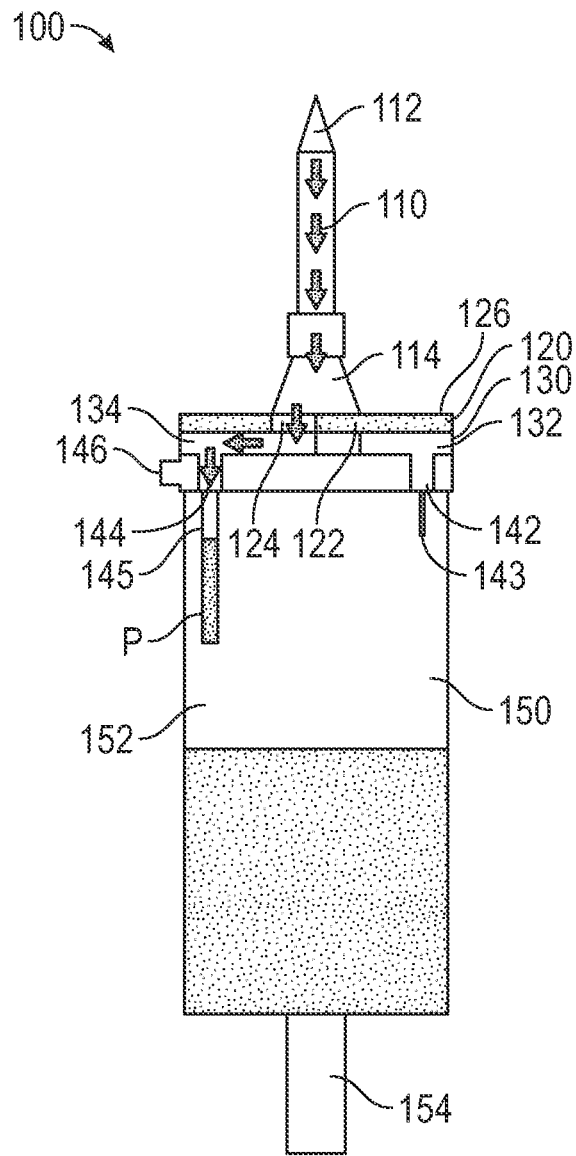
FIG. 4A
FIG. 4B

IV SET COMPONENT WITH PRIMING FUNCTION

FIELD OF THE INVENTION

The present disclosure generally relates to drip chambers or burettes, and in particular, to drip chambers or burettes with a priming configuration.

BACKGROUND

Medical treatments often include the infusion of a medical fluid (e.g., a saline solution or a liquid medication) to patients using an intravenous (IV) catheter that is connected through an arrangement of flexible tubing and fittings, commonly referred to as an "IV set," to a source of fluid, for example, an IV bag. Prior to operation, components of the IV set can be primed with medical fluid.

SUMMARY

The disclosed subject matter relates to drip chamber or burette assemblies. In certain embodiments, an IV set component is disclosed that comprises a chamber body defining a chamber volume and an outlet, wherein the chamber volume is in fluid communication with the outlet; an inlet portion coupled to the chamber body, the inlet portion defining an inlet, a priming port, a drip port, wherein the inlet is in fluid communication with the priming port and the drip port, and the priming port and the drip port are each in fluid communication with the chamber volume; and a disk valve coupled to the inlet portion, wherein the disk valve is movable to direct flow from the inlet to the priming port in a first position and to direct flow from the inlet to the drip port in a second position.

In certain embodiments, a method is disclosed that comprises introducing flow to a chamber comprising a chamber volume; directing flow into the chamber volume at a first flow rate via a priming port; moving a disk valve to direct flow from the priming port to a drip port; and directing flow into the chamber volume at a second flow rate via the drip port, wherein the second flow rate is less than the first flow rate.

In certain embodiments, an IV set is disclosed that comprises a fluid source; and an IV set component, comprising: a chamber body defining a chamber volume and an outlet, wherein the chamber volume is in fluid communication with the outlet; an inlet portion coupled to the chamber body, the inlet portion defining an inlet, a priming port, a drip port, wherein the inlet is in fluid communication with the priming port and the drip port, the priming port and the drip port are each in fluid communication with the chamber volume, and the inlet is in fluid communication with the fluid source; and a disk valve coupled to the inlet portion, wherein the disk valve is movable to direct flow from the first portion of tubing to the priming port in a first position and to direct flow from the first portion of tubing to the drip port in a second position.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 4A illustrates a cross-sectional view of the drip chamber assembly of FIG. 2 in a drip configuration.

FIG. 4B illustrates a cross-sectional view of the drip chamber assembly of FIG. 2 in a priming configuration.

DETAILED DESCRIPTION

The disclosed IV set component provides a priming flow path, a drip flow path, and a valve to direct flow between the priming flow path and the drip flow path. The IV set component selectively allows for rapid priming and a drip flow into the chamber.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to drip chambers for the administration of medical fluid using the disclosed drip chambers, it is to be understood that this description is only an example of usage and does not limit the scope of the claims. Various aspects of the disclosed drip chambers may be used in any application, such as drip chambers, in-line drip chambers, dual-input drip chambers, burettes, or other IV set components where it is desirable to provide rapid priming.

The disclosed drip chamber overcomes several challenges discovered with respect to certain conventional drip chambers. One challenge with certain conventional drip chambers is that certain conventional drip chambers may require a significant amount of time to draw in sufficient medical fluid to prime the drip chamber. Another challenge with certain conventional drip chambers is that certain conventional drip chambers require repetitive manual actions to draw in sufficient medical fluid to prime the drip chamber. Because significant priming time may delay procedures and occupy a clinician's attention and repetitive manual actions may cause clinicians to experience fatigue, the use of conventional drip chambers is not desirable.

Therefore, in accordance with the present disclosure, it is advantageous to provide a drip chamber as described herein that allows for rapid priming without requiring manual actions. The disclosed drip chamber provides a priming flow path, a drip flow path, and a valve to direct flow between the priming flow path and the drip flow path to allow for rapid priming and a drip flow, as desired.

Examples of drip chambers that allow for rapid priming and drip flow operation are now described.

Figure 1:
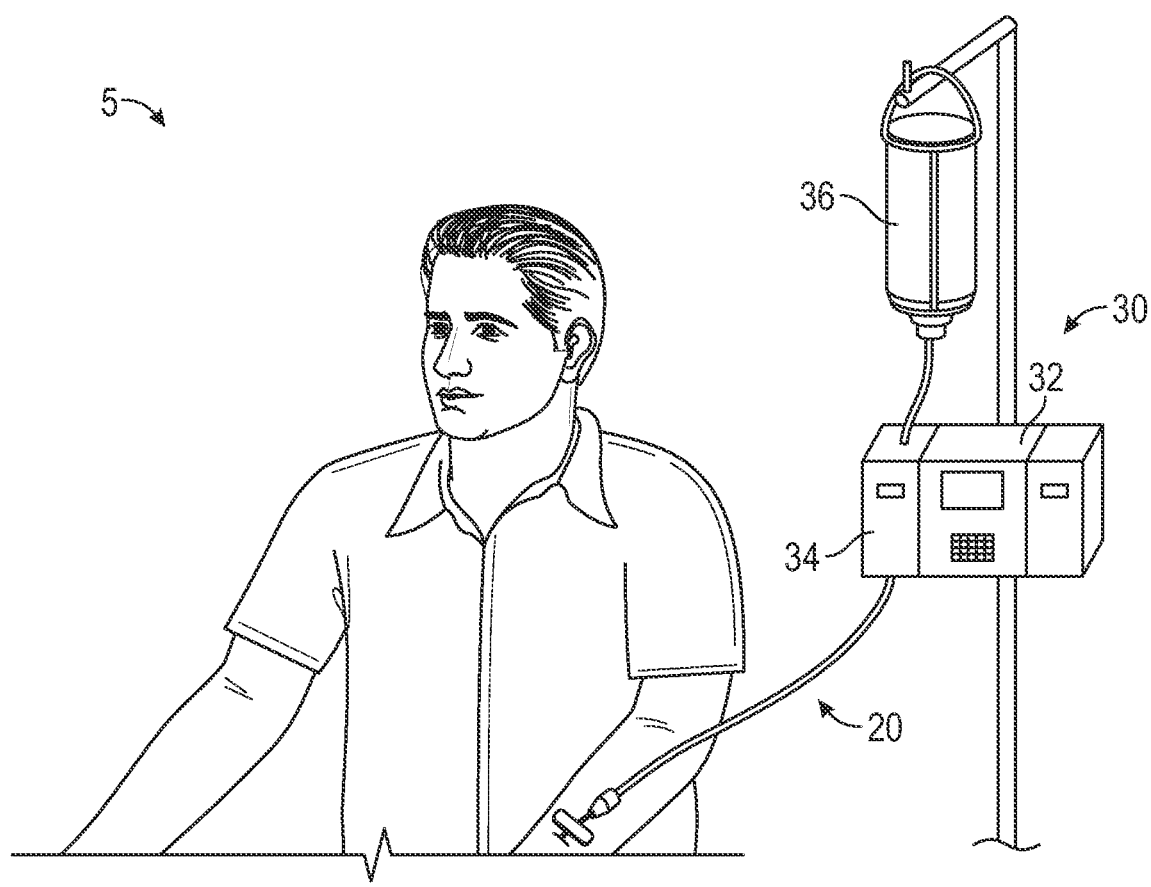
FIG. 1 depicts a patient receiving an infusion of a medical fluid using an IV pump.

FIG. 1 illustrates a patient 5 receiving an infusion of a medical fluid through an IV pump 30 according to certain aspects of the present disclosure. The IV pump 30 comprises a controller 32 and two pump modules 34. An IV set 20 is connected between a container 36 of the medical fluid and the patient 5. Prior to operation, components of the IV set 20 can be primed with medical fluid. A drip chamber assembly as described herein can allow for priming operations and delivery of the medical fluid to the patient 5. In some embodiments, a drip chamber assembly can be disposed in between or in line with tubing of the IV set 20. As can be appreciated, the drip chamber assembly can be used in other applications without the IV pump 30. For example, a drip chamber assembly can be coupled to a fluid source, such as a fluid bag.

Figure 2:
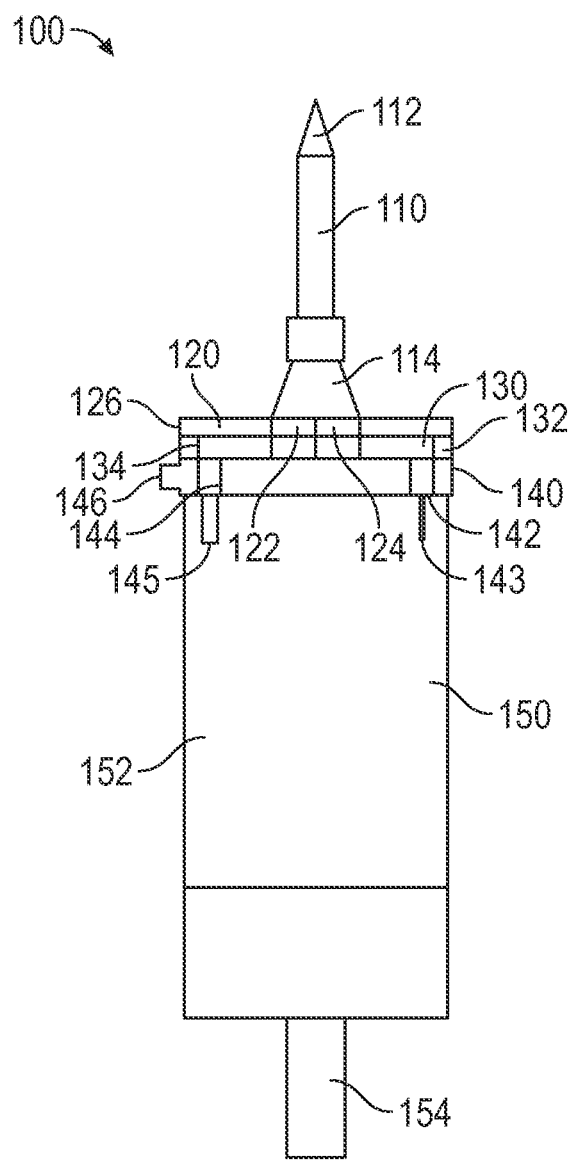
FIG. 2 illustrates a cross-sectional view of a drip chamber assembly according to certain aspects of the present disclosure.

FIG. 2 illustrates a cross-sectional view of a drip chamber 100 according to certain aspects of the present disclosure. With reference to FIG. 2, the drip chamber 100 provides a visual indicator of the flow rate of a medical fluid therethrough. Advantageously, clinicians can monitor and adjust the flow rate of the medical fluid based on the visual indicator provided by the drip chamber 100.

During operation, medical fluid can drip or otherwise flow through the chamber volume 152 defined by the chamber body 150. Medical fluid can enter the chamber body 150 through an upper portion or inlet portion 110 coupled to the chamber body 150. The inlet portion 110 can be in fluid communication with the chamber body 150 to allow medical fluid to flow from the inlet portion 110 into the chamber volume 152. The medical fluid can exit the chamber body 150 through a lower portion or outlet portion 154. The outlet portion 154 can be in fluid communication with the chamber volume 152. The inlet portion 110 and/or the outlet portion 154 can be coupled to tubing of the IV set 20.

In the depicted example, the inlet portion 110 can define an inlet channel 114 to allow medical fluid into the chamber body 150. Optionally, the inlet portion 110 can include or define a spike 112 to pierce membranes, such as an IV container membrane. In some embodiments, the inlet channel 114 can be formed through the spike 112 extending from the inlet portion 110.

As fluid passes through the chamber body 150, a clinician can utilize the drip chamber 100 as a visual indicator to observe the dripping or flow of medical fluid therethrough. As can be appreciated the chamber body 150 can be transparent or semi-transparent to allow the clinician to view the dripping or flow of medical fluid within the chamber volume 152.

In the depicted example, the drip chamber 100 can allow for medical fluid to drip within the chamber body 150 at a controlled drip rate. During operation, the medical fluid can flow from the inlet channel 114 to a drip port 142 formed in the inlet portion 110. The drip port 142 can be sized, shaped, or otherwise configured to provide a desired drop or flow rate into the chamber body 150. In some embodiments, the drip port 142 can be coupled to a drop former 143 to allow for droplets to be readily formed within the drip chamber 100. As can be appreciated, the flow rate of the medical fluid through the drip port 142 can be configured to provide a suitable medical flow for a desired operation (e.g. 20 drops per minute).

In some embodiments, the medical fluid can flow from the inlet channel 114 to the drip port 142 via a manifold 130 formed within the inlet portion 110. As illustrated, the manifold 130 can include or define a drip flow path 132 to direct flow from the inlet channel 114 to the drip port 142.

Further, in the depicted example, the drip chamber 100 can draw in medical fluid for priming of an IV system. As can be appreciated, the chamber volume 152 can be filled with a desired volume of medical fluid during the priming operation. In some embodiments, the chamber volume 152 can be filled to be approximately half to two-thirds of the total capacity of the chamber volume 152.

During priming, the drip chamber 100 can allow for medical fluid to flow into the chamber body 150 at an accelerated or greater flow rate compared to the flow rate of the drip port 142. In the depicted example, the medical fluid can flow from the inlet channel 114 to a priming port 144 formed in the inlet portion 110. The priming port 144 can be sized, shaped, or otherwise configured to desired flow rate into the chamber body 150. In some embodiments, the priming port 144 can include an extended outlet portion 145.

In some embodiments, the medical fluid can flow from the inlet channel 114 to the priming port 144 via a priming flow path 134 defined within the manifold 130. The priming flow path 134 can direct flow from the inlet channel 114 to the priming port 144.

In some embodiments, the drip chamber 100 can include vent port 146 to equalize pressure differentials between the chamber volume 152 and the environment during priming operations. The vent port 146 can provide fluid communication between the priming port 144, the chamber volume 152, and/or the environment to equalize pressure differentials. Advantageously, by allowing for the pressure within the chamber volume 152 to be equalized with the environment during priming, the flow rate through the priming port 144 can be increased relative to the flow rate through the drip port 142.

The vent port 146 can be in fluid communication with the priming flow path 134 of the manifold 130. The vent port 146 can equalize a pressure differential between the environment and the priming flow path 134 during a priming operation.

Figure 3:
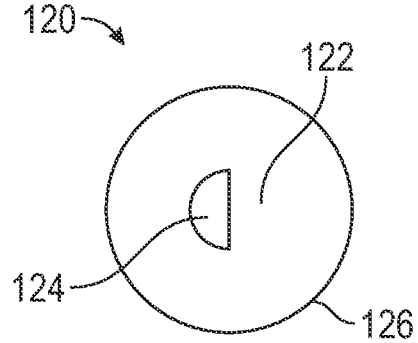
FIG. 3 illustrates a top view of a disk valve of the drip chamber assembly of FIG. 2.

In the depicted example, the drip chamber 100 can be configured to allow for drip flow during normal operation and for increased priming flow during priming operations. FIG. 3 illustrates a top view of a disk valve 120 of the drip chamber 100 of FIG. 2. With reference to FIGS. 2 and 3, the disk valve 120 can direct flow from the inlet channel 114 to the drip port 142 for drip operation or to the priming port 144 for priming operation.

During operation, the disk valve 120 is movable to direct flow from the inlet channel 114 toward the drip port 142 or the priming port 144. As illustrated, the disk valve 120 defines a flow portion 124 that permits flow to pass therethrough. The flow portion 124 can be shaped or otherwise configured to direct flow from the inlet channel 114 toward the drip port 142 and/or the priming port 144. The disk valve 120 further defines a seal portion 122 that is shaped to prevent or block flow from the inlet channel 114 to the drip port 142 and/or the priming port 144.

In the depicted example, the flow portion 124 and the seal portion 122 of the disk valve 120 can be moved or aligned to control the flow from the inlet channel 114 and the operation of the drip chamber 100. The disk valve 120 can be slid, translated, rotated, or otherwise actuated to adjust the position of the disk valve 120.

FIG. 4A illustrates a cross-sectional view of the drip chamber 100 of FIG. 2 in a drip configuration. With reference to FIGS. 2-4A, the disk valve 120 can be moved to allow the drip chamber 100 to operate in a drip configuration. In the depicted example, the disk valve 120 can be moved to align the flow portion 124 to direct flow from the inlet channel 114 toward the drip port 142. As illustrated, the flow portion 124 can direct flow from the inlet channel 114 through the drip flow path 132 to the drip port 142, permitting drip flow F to accumulate in the chamber volume 152. Further, the seal portion 122 can be aligned to prevent flow from the inlet channel 114 toward the priming port 144. As illustrated, the seal portion 122 can seal the priming flow path 134 to prevent flow from the inlet channel 114 from entering the priming port 144.

FIG. 4B illustrates a cross-sectional view of the drip chamber 100 of FIG. 2 in a priming configuration. With reference to FIGS. 2, 3, and 4B, the disk valve 120 can be moved to allow the drip chamber 100 to operate in a priming configuration. In the depicted example, the disk valve 120 can be moved to align the flow portion 124 to direct flow from the inlet channel 114 toward the priming port 144. As illustrated, the flow portion 124 can direct flow from the inlet channel 114 through the priming flow path 134 to the priming port 144, permitting priming flow P to accumulate in the chamber volume 152. Further, the seal portion 122 can be aligned to prevent flow from the inlet channel 114 toward the drip port 142. As illustrated, the seal portion 122 can seal the drip flow path 132 to prevent flow from the inlet channel 114 from entering the drip port 142.

As described herein, the disk valve 120 can be moved to change the drip chamber 100 between the drip configuration and the priming configuration. The disk valve 120 can be slid, translated, rotated, or otherwise actuated to adjust the position of the disk valve 120. In some embodiments, the disk valve 120 is rotatable relative to the inlet portion 110. Optionally, an outer portion 126 of the disk valve 120 can be rotated to move or otherwise actuate the disk valve 120 and adjust the position of the flow portion 124 and/or the seal portion 122 of the disk valve 120.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. An IV set component, comprising:
a chamber body defining a chamber volume and an outlet, wherein the chamber volume is in fluid communication with the outlet;
an inlet portion coupled to the chamber body, the inlet portion defining an inlet, a priming port, a drip port, wherein the inlet is in fluid communication with the priming port and the drip port, and the priming port and the drip port are each in fluid communication with the chamber volume; and
a disk valve coupled to the inlet portion, wherein the disk valve defines a flow portion configured to permit flow therethrough and a seal portion configured to prevent flow therethrough and the disk valve is movable to (i) align the flow portion of the disk valve with the priming port to direct flow from the inlet to the priming port and to align the seal portion of the disk valve with the drip port to obstruct flow to the drip port in a first position and (ii) to direct flow from the inlet to the drip port in a second position.

2. The IV set component of claim 1, wherein the priming port is configured to direct flow into the chamber volume at a first flow rate, the drip port is configured to direct flow into the chamber volume at a second flow rate, and the first flow rate is greater than the second flow rate.

3. The IV set component of claim 1, wherein the inlet portion further defines a vent port, wherein the vent port is in fluid communication with the priming port and the chamber volume and is configured to vent gas from the chamber volume.

4. The IV set component of claim 1, wherein the flow portion is aligned with the drip port to permit fluid communication between the inlet and the drip port and the seal portion is aligned with the priming port to prevent fluid communication between the inlet and the priming port in the second position.

5. The IV set component of claim 1, wherein the disk valve comprises an outer portion disposed around the flow portion and the seal portion, configured to permit a user to move the disk valve.

6. The IV set component of claim 1, wherein the flow portion and the seal portion of the disk valve are rotatable or translatable relative to the inlet portion.

7. The IV set component of claim 1, wherein the inlet portion further defines a drop former in fluid communication with the drip port.

8. The IV set component of claim 1, wherein the inlet portion comprises:
a manifold defining a priming flow path between the inlet and the priming port and a drip flow path between the inlet and the drip port.

9. The IV set component of claim 8, wherein the disk valve is movable to direct flow to the priming flow path in the first position and to direct flow to the drip flow path in the second position.

10. An IV set, comprising:
a fluid source; and
an IV set component, comprising:
a chamber body defining a chamber volume and an outlet, wherein the chamber volume is in fluid communication with the outlet;
an inlet portion coupled to the chamber body, the inlet portion defining an inlet, a priming port, a drip port, wherein the inlet is in fluid communication with the priming port and the drip port, the priming port and the drip port are each in fluid communication with the chamber volume, and the inlet is in fluid communication with the fluid source; and
a disk valve coupled to the inlet portion, wherein the disk valve defines a flow portion configured to permit flow therethrough and a seal portion configured to prevent flow therethrough and the disk valve is movable to (i) align the flow portion of the disk valve with the priming port to direct flow from the fluid source to the priming port and align the seal portion of the disk valve with the drip port to obstruct flow to the drip port in a first position and (ii) to direct flow from the fluid source to the drip port in a second position.

11. The IV set of claim 10, wherein the priming port is configured to direct flow from the fluid source into the chamber volume at a first flow rate, the drip port is configured to direct flow from the fluid source into the chamber volume at a second flow rate, and the first flow rate is greater than the second flow rate.

12. The IV set of claim 10, wherein the inlet portion further defines a vent port, wherein the vent port is in fluid communication with the priming port and the chamber volume and is configured to vent gas from the chamber volume.

* * * * *